(12) United States Patent
Sokol et al.

(10) Patent No.: US 6,270,777 B1
(45) Date of Patent: Aug. 7, 2001

(54) CONSERVED METALLOPROTEASE EPITOPES

(75) Inventors: Pamela A. Sokol; Cora D. Kooi, both of Calgary (CA)

(73) Assignee: University Technologies International Inc. (CA)

( * ) Notice: Subject to any disclaimer, the term of this patent is extended or adjusted under 35 U.S.C. 154(b) by 0 days.

(21) Appl. No.: 08/772,282

(22) Filed: Dec. 20, 1996

(51) Int. Cl.$^7$ .................. A61K 39/104; A61K 39/02; C07K 14/195; C07K 14/21
(52) U.S. Cl. ................... 424/260.1; 424/184.1; 424/190.1; 424/234.1; 424/130.1; 424/94.67; 424/261.1; 424/246.1; 424/185.1; 424/197.11; 530/300; 530/324; 530/325; 530/326; 530/327; 530/328; 530/350; 530/387.1
(58) Field of Search ................ 424/234.1, 260.1, 424/261.1, 246.1, 190.1, 184.1, 185.1, 197.11, 130.1, 94.67; 530/300, 324–328, 350, 387.1; 514/2

(56) References Cited

U.S. PATENT DOCUMENTS 5,445,818 * 8/1995 Hodges et al. .

FOREIGN PATENT DOCUMENTS

2104285 * 4/1990 (JP) .
9318054 * 9/1993 (WO) .

OTHER PUBLICATIONS

Wretland, B., and O.R. PavloVskis (1983), Rev. Infect. Dis. 5 (Suppl.): 998–1004.
Hong, Y.Q., and Ghebrehiwet, B. (1992), Clin. Immunol. Immunopathol. 62:133–138.
Horvat, R.T. and M.J. Parmely (1988), Infect. Immun. 56:2925–2932.
Kessler, E., M. Safrin, J.C. Olson and D.E. Ohman (1993), J. Biol. Chem. 268:7503–7508.
Olson, J.C. and D.E. Ohman (1992), J. Bacteriol., 174:4140–4147.
Toder, D.S., S.J. Ferrell, J.L. Nezezon, L. Rust, and B.H. Iglewski (1994), Infect. Immun. 62:1320–1327.
Kooi, C., A. Cox, P. Darling, and P.A. Sokol (1994), Infect. Immun., 62:2811–2817.
Bever, R.A., and B.H. Iglewski (1988), J. Bacteriol., 170:4309–4314.
Towbin, H., T. Staehelin, and J. Gordon (1979), Proc. Natl. Acad. Sci. USA, 76:4350–4354.
Booth, B.A., M. Boesman–Finkelstein, and R. Finklestein, (1983), Infect. Immun., 42:639–644.
Finkelstein, R.A., M. Boseman–Finkelstein, and P. Holt, (1983), Proc. Natl. Acad. Sci. USA, 80:1092–1095.
Hase, C.C., and R.A. Finkelstein, (1990), Infect. Immun., 58:5011–4015.
Hase, C.C., and R.A. Finkeltein, (1991), J. Bacteriol., 173:3311–3317.
Hase, C.C., and R.A. Finkelstein, (1993), Microbiol. Reviews, 57:823–837.
Gilligan P.H. (1991), Clin. Microbiol. Rev., 4:35–51.
Peques, D.A. et al, (1993), Clin. Infect. Dis., 16:407–11.
Taylor, R.F.H. et al, (1993), Resp. Medicine, 87:187–192.
McKevitt, A.L. and D.E. Woods (1984), J. Clin. Micro., 19:291–293.
McKevitt, A.L. et al, (1989), Infect. Immun., 57:771–778.
Fick, R.B. Jr., et al, (1985), J. Inf. Dis., 151:589–598.
Bainbridge, T. and R.B. Fick, Jr., (1989), J. Clin Lab. Med., 114:728–733.
Horvat, R.T., et al (1989), Infect. Immun., 57:1668–1674.
Klinger, J.D., et al (1978), J. Inf. Dis., 138:49–58.
Jagger, K.S. et al, (1982), J. Clin. Micro., 15:1054–1058.
Doring, G. et al, (1983), J. Inf. Dis., 147:744–750.
Hollsing, A.E., et al, (1987), J. Clin. Microbiol., 25:1868:1874.
Granstrom, M. et al, (1984), Acta. Paediatr. Scand., 73:772–777.
Jongeneel, C.V. et al, (1989), FEBS Lett., 242:211–214.
Kooi, C., and P.A. Sokol, (1996), J. Med. Microbiol., In Press, 45:219–225.
Thayer, M.M. et al, (1991), J. Biol. Chem., 266:2864–2871.

* cited by examiner

Primary Examiner—Paula K. Hutzell
Assistant Examiner—Khalid Masood
(74) Attorney, Agent, or Firm—Burns, Doane, Swecker & Mathis, L.L.P.

(57) ABSTRACT

The present invention provides immunogenic compositions comprising peptides derived from the amino acid sequence of *P. aeruginosa* for protecting susceptible hosts against diseases caused by bacterial pathogens which secrete a zinc metalloprotease.

15 Claims, 5 Drawing Sheets

FIGURE 2

| Protease | Peptide 15 | Peptide 42 |
|---|---|---|
| P. aeruginosa elastase | 341 H G F T E Q N S G 349 | 395 R Y M D Q P S R D 403 |
| V. choleae HA/protease | 347 H G F T E Q N S G 355 | 401 R Y F D Q P S R D 409 |
| Thermolysin | 146 H A V T D Y T A G 154 | 203 R S M S D P A K Y 211 |
| Thermolysin | 227 N G V H I N S G 235 | 192 V Y T P G I S G D 200 |
| Alkaline protease | 224 S Y W E E Q N T G 232 | 238 A Y S S A P L L D 246 |
| Serratia SMP | 118 I T F T E V A A G 126 | 261 L Y G A N P S T R 269 |
| Serratia SMP |  | 245 H Y A A A P L L D 253 |

CONSERVED METALLOPROTEASE EPITOPES

FIELD OF THE INVENTION

The present invention relates to the field of immunization against bacterial diseases. In particular, it relates to immunization against diseases caused by bacteria which secrete zinc metalloproteases and to therapeutic vaccines for treatment of such diseases.

BACKGROUND OF THE INVENTION

In the description which follows, references are made to certain literature citations which are listed at the end of the specification.

Many bacteria produce and secrete zinc metalloproteases. For example, *Pseudomonas aeruginosa* produces at least two zinc metalloproteases, elastase and alkaline protease. Elastase degrades several important biological substances including elastin, immunoglobulins, collagen, transferrin and complement components (1). Alkaline protease has been shown to degrade C1q and C3 proteins of serum complement (2) and gamma interferon (3) *P. aeruginosa* also secretes Las A protease, which has both elastolytic and staphylolytic activity and has some properties of a metalloprotease (4–6).

*Burkholderia (Pseudomonas) cepacia* produces both a 36 kDa zinc metalloprotease (PSCP) which is immunologically related to elastase and a related 40 kDa protease (7).

*Bacillus thermoproteolyticus* secretes thermolysin, a heat-stable neutral zinc metalloprotease. There is 28% sequence homology between *P. aeruginosa* elastase and thermolysin (8), with greater homology in certain regions, particularly around the active site. However, comparison of the three-dimensional structures of thermolysin and *P. aeruginosa* elastase reveals a striking similarity (9).

*Vibrio cholerae* secretes a 33 kDa zinc metalloprotease, HA/protease, (10) which can cleave biologically important substrates such as mucin, fibronectin and bactoferritin (11). Hase and Finkelstein (12,13) have demonstrated that the *V. cholerae* HA/protease is related to *P. aeruginosa* elastase.

The bacterial metalloproteases have been shown to contribute to the virulence of many pathogenic organisms (14) which cause serious health problems.

For example, pulmonary dysfunction as a result of chronic airway infection is responsible for the vast majority of deaths in cystic fibrosis (CF) patients (15). Despite advances in microbial therapy, the treatment and prevention of infections due to *P. aeruginosa* and *B. cepacia* remains a clinical challenge (15). Although major efforts are underway to develop gene therapy as a treatment for CF patients, the practical applications of gene therapy and potential for success may not be determined for some time. Other avenues of infection control continue to be an important area for investigation.

*P. aeruginosa* has been reported to be present in 60% of respiratory tract cultures from CF patients and once colonization has occurred, *P. aeruginosa* is difficult or impossible to eradicate (16). A large array of virulence factors have been identified and shown to contribute to the pathogenesis of *P. aeruginosa* infections. These include elastase, alkaline protease, exotoxin A, exoenzyme S, pyochelin, pyoverdin, phospholipase C, pili, outer membrane proteins, lipopolysaccharide (LPS) and alginate.

*B. cepacia* is a nosocomial pathogen which has been isolated with increasing frequency from respiratory infections in CF patients over the past 20 years (15). Acquisition of *B. cepacia* can pose particular problems because of its resistance to many anti-pseudomonal antibiotics. For example, in one study of 55 CF patients with *B. cepacia* pulmonary infection, 39 (70%) had acquired multiresistant strains (17). Once acquired, *B. cepacia* is nearly impossible to eradicate.

The majority of strains (90%) of *B. cepacia* are protease positive (18). Proteases appear to be the major extracellular virulence factors produced by *B. cepacia*. McKevvit et al. (19) isolated a zinc metalloprotease, designated PSCP, which was produced by 90% of *B. cepacia* CF isolates. This protease was shown to degrade casein, gelatin, collagen, but not elastin and to cause bronchopneumonia when instilled intratracheally into rats (19).

Besides having a direct role in tissue destruction and injury, bacterial proteases such as elastase can function to modulate the host immune system and assist the bacterium in evading host defences (20–22).

Numerous studies since the late 1970's have analyzed the presence of serum antibodies to several *P. aeruginosa* antigens in CF patients (23–27). These studies all conclude that CF patients make antibodies to a variety of *P. aeruginosa* antigens and that elevated titres generally correlate with severity of disease.

Although CF patients produce high levels of antibodies to *P. aeruginosa*, several studies have indicated that these antibodies are not effective in clearance of the organism from the lungs.

These studies indicate that there remains a need for therapeutic strategies to improve the production of effective antibodies to combat infections with organisms such as *P. aeruginosa* and *B. cepacia*.

SUMMARY OF THE INVENTION

The inventors have identified two regions of the *P. aeruginosa* elastase amino acid sequence, and within these regions, two epitopes, which are recognized by antibodies which neutralise the proteolytic activity of *P. aeruginosa* elastase and other thermolysin-like proteases.

Many pathogenic organisms secrete zinc metalloproteases which are thermolysin-like and their virulence is related to secretion of these enzymes.

Peptides corresponding to the two identified regions of amino acid sequence, and peptides comprising fragments of these sequences, provide immunogenic compositions which can be administered to a host to stimulate production of neutralising antibodies and protect the host against diseases caused by pathogens which secrete thermolysin-like metalloproteases.

Antibodies raised against the peptides of the invention also recognise serralysin-like proteases and immunization with these peptides may also be used to provide protection against pathogens secreting serralysin-like proteases.

In accordance with one embodiment, the invention provides a peptide comprising the amino acid sequence VSHGFTEQNSGLIYRGQSGGMNEAF (Sequence ID NO:1)

or a fragment or analogue thereof.

In accordance with a further embodiment, the invention provides a peptide comprising the amino acid sequence HGFTEQNSG (Sequence ID NO:3).

In accordance with a further embodiment, the invention provides a peptide comprising the amino sequence SGALRYMDQPSRDGRSIDM (Sequence ID NO:11)

or a fragment or analogue thereof.

In accordance with a further embodiment, the invention provides a peptide comprising the amino acid sequence RYMDQPSRD (Sequence ID NO:14).

In accordance with a further embodiment, the invention provides an immunogenic composition comprising at least one active component selected from the group consisting of:
(a) a peptide comprising the amino acid sequence HGFTEQNSG;
(b) a peptide comprising the amino acid sequence RYMDQPSRD;
(c) a peptide comprising the amino acid sequence VSHGFTEQNSGLIYRGQSGGMNEAF;
(d) a peptide comprising the amino acid sequence SGALRYMDQPSRDGRSIDM;
(e) a fragment or analogue of a peptide of (a), (b), (c) or (d);
(f) a purified and isolated nucleic acid molecule encoding a peptide of (a), (b), (c) or (d); and
(g) a nucleotide sequence which hybridises under stringent conditions to any of the nucleic acid molecules of (f)

and a pharmaceutically acceptable carrier, the at least one active component producing an immune response when administered to a host.

In accordance with a further embodiment, the invention provides an antibody or antiserum specific for a peptide selected from the group consisting of
(a) VSHGFTEQNSGLIYRGQSGGMNEAF;
(b) SGALRYMDQPSRDGRSIDM;
(c) HGFTEQNSG;
(d) RYMDQPSRD; and
(e) a fragment or analogue of a peptide of (a), (b), (c) or (d).

In accordance with a further embodiment, the invention provides a method for protecting a susceptible host against a disease caused by a bacterial pathogen which secretes a zinc metalloprotease.

In accordance with a further embodiment, the invention provides a purified isolated nucleic acid molecule encoding a peptide selected from the group consisting of
(a) VSHGFTEQNSGLIYRGQSGGMNEAF;
(b) SGALRYMDQPSRDGRSIDM;
(c) HGFTEQNSG;
(d) RYMDQPSRD; and
(e) a fragment or analogue of a peptide of (a), (b) , (c) or (d).

In accordance with a further embodiment, the invention provides a method of producing a vaccine comprising administering an immunogenic composition comprising at least one active component selected from the group consisting of:
(a) a peptide comprising the amino acid sequence HGFTEQNSG;
(b) a peptide comprising the amino acid sequence RYMDQPSRD;
(c) a peptide comprising the amino acid sequence VSHGFTEQNSGLIYRGQSGGMNEAF;
(d) a peptide comprising the amino acid sequence SGALRYMDQPSRDGRSIDM;
(e) a fragment or analogue of a peptide of (a), (b), (c) or (d);
(f) a purified and isolated nucleic acid molecule encoding a peptide of (a), (b), (c) or (d); and
(g) a nucleotide sequence which hybridises under stringent conditions to any of the nucleic acid molecules of (f)

and a pharmaceutically acceptable carrier to a test host to determine an amount and a frequency of administration of the active component to confer protection against a disease caused by a bacterial pathogen which secretes a zinc metalloprotease, and formulating the active component in a form suitable for administration to a host to be treated in accordance with the determined amount and frequency of administration.

SUMMARY OF THE DRAWINGS

Certain embodiments of the invention are described, reference being made to the accompanying drawings, wherein:

FIG. 2 shows a sequence comparison of *P. aeruginosa* elastase peptide 15 and peptide 42 with other metalloproteases. The regions of metalloproteases with the greatest identity to peptide 15 and peptide 42 were identified using the Pc/Gene QG Search program (Intelligenetics). Identical residues are boxed. Conservative amino acid changes are underlined.

HGFTEQNSG=Sequence ID NO:3; RYMDQPSRD= Sequence ID NO. 14; RYFDQPSRD=Sequence ID NO. 20; HAVTDYTAG=Sequence NO. 21; RSMSDPAKY= Sequence NO. 22; NGGVHINSG=Sequence NO. 23; VYTPGISGD=Sequence NO. 24; SYWEEQNTG= Sequence NO. 25; AYSSAPLLD=Sequence NO. 26; ITFTEVAAG=Sequence NO. 27; LYGANPSTR=Sequence NO. 28; HYAAAPLLD=Sequence NO. 29.

Figure 3:
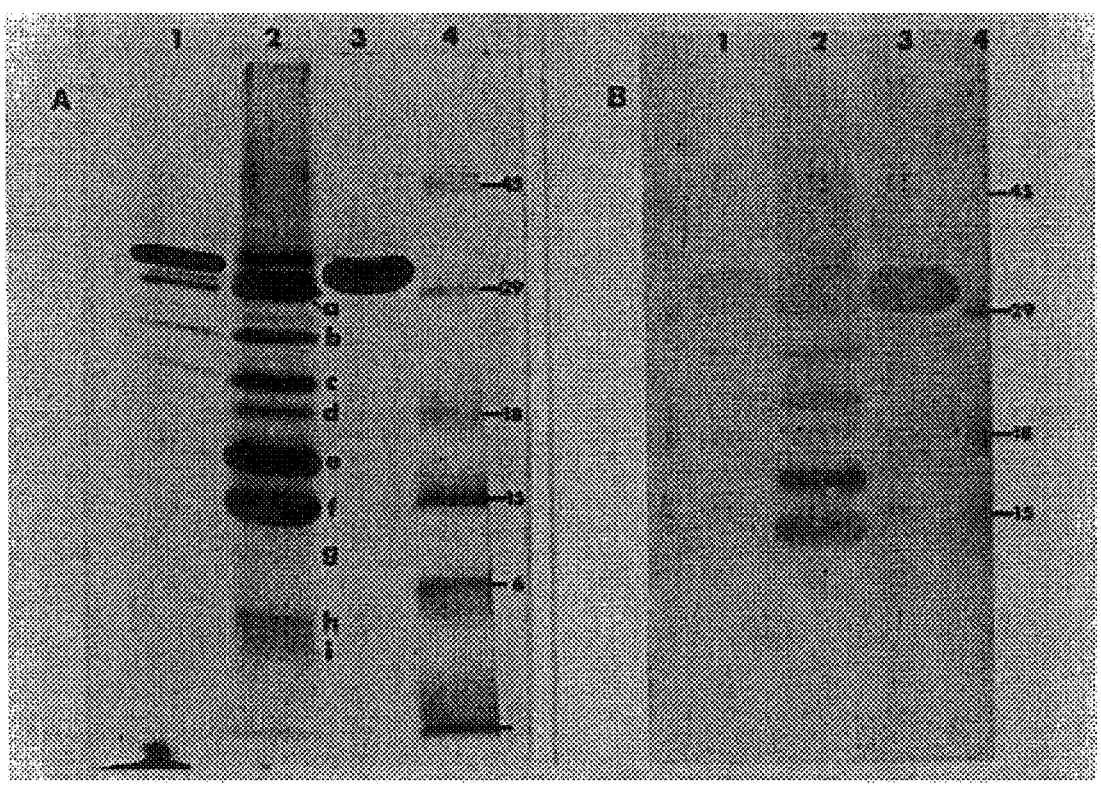

FIG. 3A shows an SDS-PAGE analysis of peptides resulting from the partial digestion of *P. aeruginosa* elastase with NCS. Peptides are stained with Coomassie blue. Lane 1: elastase digested for 1 min with NCS; Lane 2: elastase digested for 60 min with NCS; Lane 3: elastase incubated in buffer without NCS for 60 min; Lane 4: molecular mass markers: 45.5, 29.6, 18.7, 15.5, 5.9, and 2.9 kDa.

FIG. 3B shows an immunoblot analysis of NCS-elastase fragments probed with MAb 36-6-8, an antibody to *B. cepacia* 36 kDa protease. Lanes are the same as in FIG. 3A.

Figure 4:
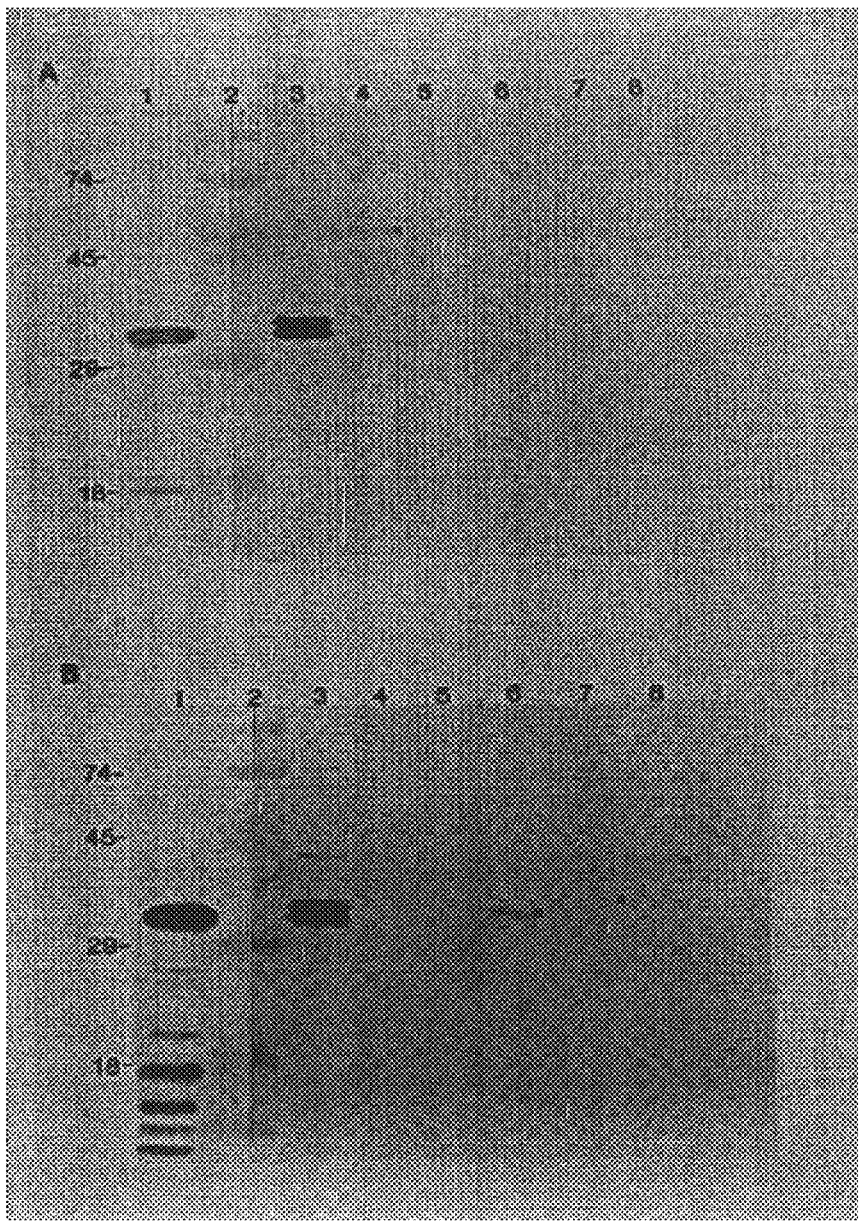

FIG. 4A shows an immunoblot of antiserum to peptide 15 binding to various bacterial metalloproteases: Lane 1, elastase; lane 2, molecular mass markers; lane 3, *V. cholerae* HA/protease; lane 4, *P. aeruginosa* alkaline protease; lane 5, SMP; lane 6, thermolysin; lane 7, *B. cepacia* PSCP; lane 8, *B. cepacia* 40 kDa protease.

FIG. 4B shows immunoblot of antiserum to peptide 42 binding to bacterial metalloproteases as in FIG. 4A.

FIG. 5A shows a comparison of ELISA binding curves of peptide 15 antibodies to the following proteases:

PSCP (■)

P. aeruginosa Elastase (▲)

Thermolysin (▼)

HA/protease (●)

40 kDa B. cepacia protease (○)

Alkaline protease (□)

SMP (Δ)

FIG. 5B shows a comparison of ELISA binding curves of peptide 42 antibodies to various proteases identified as in FIG. 5A.

DETAILED DESCRIPTION OF THE INVENTION

The zinc-dependent metalloproteases have been classified into two groups on the basis of their structure and secretion mechanism (14). The thermolysin-like or elastase-like group includes B. thermoproteolyticus thermolysin, P. aeruginosa elastase, PSCP and V. cholerae HA/protease. The serralysin-like group includes P. aeruginosa alkaline protease and Serratia marcescens protease.

The zinc metalloproteases share a unique amino acid motif HExxH (28).

Monoclonal antibodies raised against PSCP have been described (7,29) which neutralize the proteolytic activity of PSCP, P. aeruginosa elastase, thermolysin, and V. cholerae HA/protease but not P. aeruginosa alkaline protease nor Serratia marcescens SMP. These antibodies were used to determine which epitopes on these proteases were recognized by these broadly crossreactive antibodies. A combination of N-chlorosuccinimide cleavage to generate peptides, followed by overlapping synthetic peptide scanning analysis, was used to map the neutralizing epitopes. The neutralizing epitopes were mapped on P. aeruginosa elastase.

Figure 1:
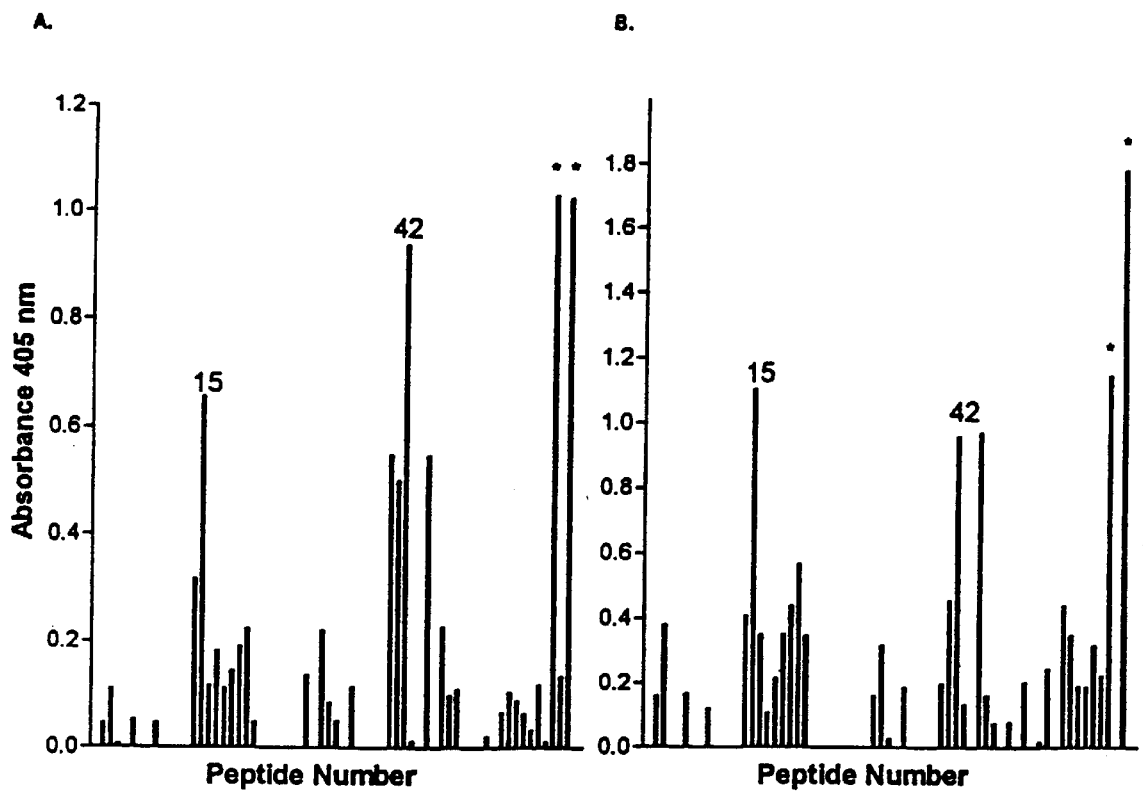
FIGS. 1A and 1B illustrate epitope mapping of a 13.9 kDa NCS-elastase fragment by peptide scanning analysis, as shown by ELISA reactions of MAb 36-6-6 (FIG. 1A) and MAb 36-6-8 (FIG. 1B) with sixty overlapping 9-mer peptides, with a two amino acid offset, encompassing the 13.9 kDa NCS-elastase fragment. Positive control peptides are indicated by asterisks.

All antibodies examined reacted strongly with peptides from two stretches of the P. aeruginosa elastase amino acid sequence, amino acids $_{339}$VSHGFTEQNSGLIYRGQSG-GMNEAF$_{363}$ and $_{391}$SGALRYMDQPSRDGRSIDM$_{409}$. Table 1 shows the overlapping 9 mer peptides within each of these stretches which reacted with the antibodies, namely peptides 14 to 22 for amino acids 339 to 363 and peptides 40–45 for amino acids 391 to 409. FIG. 1 shows the epitope mapping results.

All of the antibodies reacted most strongly with peptide 15 ($_{341}$HGFTEQNSG$_{349}$) and peptide 42 ($_{395}$RYMDQPSRD$_{403}$).

Peptide 15 overlaps the $_{337}$HExxH$_{341}$ active site found in elastase. Antibody binding to the amino acid sequence $_{341}$HGFTEQNSG$_{349}$ would explain the ability of these antibodies to neutralize elastase. An identical sequence is found in V. cholerae HA/protease (FIG. 2). Three of nine residues match the thermolysin sequence in the region of the HExxH motif, which may be sufficient for antibody binding and neutralization. A better match is found, however, in the region spanning residues 227–235, with four of nine residues identical to peptide 15. This region spans the Histidine at residue 231, which acts as a proton donor at the active site. Antibody binding to this epitope may be the reason that thermolysin is inactivated.

Peptide 42 ($_{395}$RYMDQPSRD$_{403}$) is located between $E_{361}$, which binds a zinc atom, and $H_{420}$, which acts as a proton donor at the active site (8, 30). The binding of antibodies to this epitope could effectively inhibit proteolytic activity by directly blocking the active site cleft. A nearly identical sequence is present in V. cholerae HA/protease, with eight of nine residues identical (FIG. 2). There is less homology between elastase and thermolysin in this region. Two possible epitopes recognized by the antibodies are between residues 192–200 and residues 203–211 of elastase. Both epitopes match peptide 42 with three of nine residues identical. Both sequences are located between the zinc binding site and the $H_{231}$ which serves as the proton donor.

Antibodies to peptide 15 or peptide 42 do not neutralize alkaline protease. The sequence with the best homology to peptide 15 spans residues 224–232 of alkaline protease, with four identical and two conserved residues (FIG. 2). This epitope is downstream of the active site and therefore, antibody binding to this site may have no effect on enzyme activity. Five other possible matches were identified with three identical residues (data not shown). Similarly, the best sequence match to peptide 42 lies between residues 238–246 of alkaline protease with only three residues conserved. This epitope is also downstream of the active site. There is no homology in the active site region.

Similar results were observed with Serratia SMP, which is closely related to alkaline proteases. A sequence with five of nine conserved residues with peptide 15 occurs between residues 118 and 126, which is upstream of the active site. Two sequences containing four of nine residues conserved with peptide 42 are found spanning amino acids 249–253 and 261–269. Although the epitopes on alkaline protease or SMP which are recognized by either the MAbs or the specific antibodies to peptides 15 and 42 have not been determined, it appears likely that these antibodies react with epitopes not in the active site region. Therefore, although the antibodies react with these proteases on immunoblots or ELISA, they do not neutralize proteolytic activity.

Monoclonal antibodies 36-6-6 and 36-6-8 to PSCP were previously shown to crossreact also with P. aeruginosa LasA, and Bacillus anthracis protective antigen (PA) and lethal factor (LF) (29). This crossreaction might be explained by sequence homology to peptides 15 and 42. There are six possible nine-mer epitopes in Las A with three residues identical to peptide 15. There is one possible epitope in LF with five conserved residues. Two possible sites with four residues conserved and five with three residues conserved are present in PA. In terms of peptide 42, there is one possible epitope in LasA with four conserved amino acids, three possible epitopes in PA with three conserved amino acids, and seven potential epitopes in LF with three conserved residues.

The ability of the antibodies to PSCP to crossreact with Legionella pneumophila protease has not been examined. However, peptide 15 and 42 sequences are well conserved in this protease with eight of nine residues identical for each peptide. Therefore, it is likely that the anti-PSCP antibodies, as well as antipeptide 15 and antipeptide 42 antibodies, would also neutralize L. pneumophila protease.

Antibody to peptide 15 and peptide 42 reacted better with nondenatured proteases in the ELISA assay than with denatured proteins on Western blots. The ability of the antibodies to react with proteases on Western blots appeared to correlate with the degree of sequence homology between the elastase epitopes corresponding to peptide 15 or 42. There was less of a difference in the ELISA reactions although both antisera, particularly antipeptide 42 sera, reacted most strongly with elastase and HA/protease.

All of the neutralizing antibodies isolated to PSCP, even though they were individual clones, reacted most strongly with peptides 15 and 42 in the overlapping synthetic peptide scanning analysis. Antibodies to either of these peptides were determined to be sufficient for neutralization of elastase, PSCP, HA/protease and thermolysin in vitro.

The various embodiments of the present invention enable many applications for treatment of and vaccination against pathogenic bacterial species which secrete zinc metalloproteases.

For bacterial species whose virulence is related to secreted thermolysin-like proteases, stimulation of an antibody response to the peptides of the invention, as described further below, will provide neutralising antibodies which combat the destructive proteolytic activity of the secreted proteases.

Such bacterial species include pathogens of humans and other mammals and also pathogens of other vertebrates such as fish; for example such species include strains of *P. aeruginosa, B. cepacia, Vibrio cholerae, V. anguillarum, V. vulnificus, Legionella pneumophila, Staphylococcus epidermidis,* and *S. aureus.*

For bacterial species which produce and secrete serralysin-like proteases, which may not be neutralized by antibodies stimulated by the peptides of the invention, a protective effect may nevertheless be achieved where these antibodies bind to protease molecules on the bacterial cell surface, leading to opsonic and phagocytic destruction of the bacteria. Such bacterial species include strains of *S. marcescens* and *Aeromonas hydrophila.*

For bacterial species which produce thermolysin-like proteases, which may be neutralized by antibodies stimulated by the peptides of the invention, an additional protective effect may be achieved where these antibodies bind to protease molecules on the bacterial cell surface, leading to opsonic and phagocytic destruction of the bacteria. Such bacterial species include strains of *P. aeruginosa, B. cepacia, Vibrio cholerae, V. anguillarum, V. vulnificus, Legionella pneumophila, Staphylococcus epidermidis,* and *S. aureus.*

For bacterial species which produce zinc metalloproteases which may not have yet been classified, antibodies stimulated by the peptides of the invention may provide neutralizing antibodies and/or opsonophagocytic activity leading to the destruction of the bacteria. Such bacterial species include strains of *Bacillus anthracis, Clostridium tetani, C. botulinum, Streptococcus sanguis, S. faecalis, Pasteurella haemolytica,* and *Lysteria monocytogenes.*

1. Vaccine Preparation and Use

Immunogenic compositions, suitable to be used as vaccines, may be prepared from peptide VSHGFTEQNSGLIYRGQSGGMNEAF, peptide SGALRYMDQPSRDGRSIDM and fragments and analogues thereof, as disclosed herein.

Peptides of about nine consecutive amino acids selected from the sequences VSHGFTEQNSGLIYRGQSGGMNEAF and SGALRYMDQPSRDGRSIDM, or analogues of such peptides, are preferred.

Peptides HGFTEQNSG and RYMDQPSRD are especially preferred. An immunogenic composition may also be prepared from a peptide mixture, such as a mixture of peptides HGFTEQNSG and RYMDQPSRD.

The peptide to be used as immunogen is preferably conjugated to a carrier protein to improve its immunogenicity. Suitable carrier proteins for immunogens for human use include keyhole limpet haemocyanin, diphtheria toxoid, diphtheria toxin CRM197, tetanus toxoid, *P. aeruginosa* exotoxin A mutant form, cholera toxin B subunit, pertussis toxin subunits, measles virus F protein and Haemophilus PRP outer membrane protein.

Such immunogenic compositions elicit an immune response in a treated subject which produces antibodies, including anti-peptide 15 and/or anti-peptide 42 antibodies. If the treated subject is challenged by *P. aeruginosa, B. cepacia, Vibrio cholerae* or other bacteria that secrete a thermolysin-like metalloprotease, the antibodies elicited by the vaccination neutralise the zinc metalloprotease of the invading organism and resist tissue destruction by the organism.

Antibodies produced in a subject in response to vaccination with one of the peptides of the invention may also provide protection by means of bactericidal or opsonising properties. For example, bacteria which have on their cell surface proteases which bind to the produced antibodies may be destroyed by opsonising and phagocytosis or by bactericidal activity in the presence of complement.

Administration of the immunogenic compositions of the invention to a subject may be done either as a therapeutic measure after the subject has become infected with a zinc metalloprotease-producing pathogen, or may be done as a prophylactic measure in subjects susceptible to infection with such pathogens.

For example, chronic infections occurring in CF, pan-bronchiolitis or bronchitis may be treated therapeutically. Subjects susceptible to infections, for example cancer patients or burn patients or military personnel, may receive prophylactic immunisation.

Vaccines containing proteins or peptides are generally well known in the art, as exemplified by U.S. Pat. Nos. 4,601,903; 4,599,231; 4,599,230; and 4,596,792; all of which references are incorporated herein by reference. Immunogenic compositions including vaccines may be prepared as injectables, as liquid solutions or as emulsions. Peptide 15 or peptide 42 or analogues or fragments thereof may be mixed with pharmaceutically acceptable excipients which are compatible with the peptides, fragments or analogues. Such excipients may include water, saline, dextrose, glycerol, ethanol, and combinations thereof.

The immunogenic compositions and vaccines of the invention may further contain auxiliary substances such as wetting or emulsifying agents, pH buffering agents, or adjuvants to enhance the effectiveness of the vaccines.

Immunogenic compositions and vaccines may be administered parenterally, or by injection subcutaneously or intramuscularly. Alternatively, the immunogenic compositions formed according to the present invention may be formulated and delivered in a manner to evoke an immune response at mucosal surfaces. The oral, nasal, vaginal, gastrointestinal, respiratory or other mucosal route of vaccine administration may be preferred to combat infections which take place at mucosal surfaces, for example in the respiratory, digestive or urogenital tracts. Nasal immunization has been shown to be efficacious in generating both respiratory tract mucosal immunity and systemic immunity. Inhalation of an aerosol formulation may also be used to combat lung or respiratory tract infections.

Delivery systems for mucosal immunization include lipid vesicles, biodegradable microcapsules, attenuated bacteria, live viral vectors and bacterial toxins or subunits thereof. For examples, cholera toxin B subunit may be conjugated to an antigen for improved mucosal immunization.

Targeting molecules such as strain B12 and fragments of bacterial toxins, are described in WO92/17167 (Biotech Australia Pty. Ltd.), and targeting monoclonal antibodies are described in U.S. Pat. No. 5,194,254 (Barber et al.). Alternatively, other modes of administration including suppositories and oral formulations may be desirable. For suppositories, binders and carriers may include, for example, polyalkalene glycols or triglycerides. Oral formulations may include normally employed excipients such as, for example, pharmaceutical grades of saccharine, cellulose and magnesium carbonate. Immunogenic compositions may take the form of solutions, aerosols, suspensions, tablets, pills, capsules, sustained release formulations or powders and may comprise 10–95% of peptide 15 or peptide 42 or an analogue or fragment of one of these peptides.

The vaccines are administered in a manner compatible with the dosage formulation, and in such amount as will be therapeutically effective, protective and immunogenic. The quantity of vaccine to be administered depends on the subject to be treated, including, for example, the weight of the subject and the capacity of the subject's immune system to synthesise antibodies, and if needed, to produce a cell-mediated immune response. The dosage of the vaccine may also depend on the route of administration. However, suitable dosage ranges are readily determinable by one skilled in the art and may be of the order of micrograms of the peptides, analogues or fragments thereof. Suitable regimes for initial administration and booster doses of vaccine are also well known in the art. These include an initial administration followed by subsequent administrations.

Nucleic acid molecules encoding the peptides of the present invention may also be used for immunization. For example, DNA in a plasmid vector may be administered directly, in saline, by injection, preferably by intramuscular injection, for genetic immunization. It is believed that the DNA is expressed in vivo to give the encoded peptide antigen which stimulates an immune response. DNA may also be administered by constructing a live vector such as Salmonella, BCG, adenovirus, poxvirus, vaccinia or poliovirus including the DNA. Some live vectors that have been used to carry heterologous antigens to the immune system are discussed in, for example, O'Hagan (31). Processes for the direct injection of DNA into subjects for genetic immunization are described in, for example, Ulmer et al., (32). Nucleic acid molecules encoding the peptides of the invention may be obtained, for example, by excising the relevant portions of *P. aeruginosa* elastase DNA, clones of which are available from the group which obtained this sequence (8).

Alternatively, a nucleic acid molecule encoding a peptide of the invention conjugated to a selected carrier protein may be used for immunization, as described above.

The immunogenicity of antigens can be significantly improved if they are co-administered with adjuvants. Adjuvants may be employed which not only enhance but selectively modulate the type of immune response to the administered antigen; for example monophosphoryl lipid A (MPL) favours a TH1 type response, while QS21 (Cambridge Biotech) favours a cytotoxic T cell response.

Adjuvants or immunostimulatory agents are known to improve host immune responses to vaccines. Intrinsic adjuvants, such as lipopolysaccharides, normally are the components of the killed or attenuated bacteria used as vaccines. Aluminum hydroxide and aluminum phosphate (collectively commonly referred to as alum) are adjuvants commonly used in human and veterinary vaccines.

An adjuvant should be non-toxic, capable of stimulating a sustained immune response and compatible with the immunogenic composition employed as a vaccine.

U.S. Pat. No. 4,855,283 granted to Ockhoff et al. on Aug. 8, 1989 which is incorporated herein by reference teaches glycolipid analogues, including N-glycosylamide, N-glycosylureas and N-glycosylcarbamates, each of which is substituted in the sugar residues by an amino acid, as immuno-modulators or adjuvants. Lockhoff et al. (33) reported that N-glycolipid displaying structural similarities to the naturally occurring glycolipids, such as glycosphingolipids and glycoclycerolipids, are capable of eliciting strong immune responses both to herpes simplex virus and to pseudorabies virus. Some glycolipids have been synthesised from long chain-alkylamines and fatty acids that are linked directly with the sugars through the anomeric carbon atom, to mimic the functions of the naturally occurring lipid residues.

Lipidation of synthetic peptides has also been used to increase their immunogenicity. Thus, Wiesmuller (34), describes a peptide with a sequence homologous to a foot-and-mouth disease viral protein coupled to an adjuvant tripalmityl-s-glyceryl-cysteinylserylserine, being a synthetic analogue of the N-terminal part of the lipoprotein from Gram negative bacteria. Furthermore, Deres et al. (35), reported in vivo priming of virus-specific cytotoxic T lymphocytes with synthetic lipopeptide vaccine which comprised modified synthetic peptides derived from influenza virus nucleoprotein by linkage to a lipopeptide, N-palmityl-s-[2,3-bis(palmitylxy)-(2RD)-propyl[R]-cysteine (TPC).

2. Preparation of Peptides

Peptides in accordance with the invention or fragments or analogues thereof, may be prepared by any suitable peptide synthetic method.

Chemical synthesis may be employed, for example standard solid phase peptide synthetic techniques may be used. In standard solid phase peptide synthesis, peptides of varying length can be prepared using commercially available equipment. This equipment can be obtained from Applied Biosystems (Foster City, Calif.). The reaction conditions in peptide synthesis are optimized to prevent isomerization of stereochemical centres, to prevent side reactions and to obtain high yields. The peptides are synthesized using standard automated protocols, using t-butoxycarbonyl-alpha-amino acids, and following the manufacturer's instructions for blocking interfering groups, protecting the amino acid to be reacted, coupling, deprotecting and capping of unreacted residues. The solid support is generally based on a polystyrene resin, the resin acting both as a support for the growing peptide chain, and as a protective group for the carboxy terminus. Cleavage from the resin yields the free carboxylic acid. Peptides are purified by HPLC techniques, for example on a preparative C18 reverse phase column, using acetonitrile gradients in 0.1% trifluoroacetic acid, followed by vacuum drying.

Peptides may also be produced by recombinant synthesis. A DNA sequence encoding the desired peptide is prepared, for example by cloning the required fragment from the DNA sequence encoding elastase, and subcloning into an expression plasmid DNA. Suitable mammalian expression plasmids include pRC/CMV from Invitrogen Inc. The gene construct is expressed in a suitable cell line, such as a Cos or CHO cell line and the expressed peptide is extracted and purified by conventional methods. Suitable methods for recombinant synthesis of peptides are described in "Molecular Cloning" (Sambrook, Fritsch and Maniatis, Cold Spring Harbor Laboratory Press, 1989).

Analogues of a peptide may be prepared by similar synthetic methods. The term "analogue" extends to any functional and/or chemical equivalent of peptide 15 or peptide 42 and includes peptides having one or more conservative amino acid substitutions, peptides incorporating unnatural amino acids and peptides having modified side chains.

Examples of side chain modifications contemplated by the present invention include modification of amino groups such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with NaBH$_4$.

The guanidino group of arginine residues may be modified by the formation of heterocyclic condensation products with reagents such as 2, 3-butanedione, phenylglyoxal and glyoxal.

The carboxyl group may be modified by carbodiimide activation via -acylisourea formation followed by subsequent derivatisation, for example, to a corresponding amide.

Sulfhydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tyrosine residues may be altered by nitration with tetranitromethane to form a 3-nitrotyrosine derivative.

Modification of the imidazole ring of a histidine residue may be accomplished by alkylation with iodacetic acid derivatives of N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid-, t-butylglycine, norvaline, phenylglycine, ornithine, sarcosine, 4-amino-3-hydroxy-6-methylheptanoic acid, 2-thienyl alanine and/or D-isomers or amino acids.

Examples of conservative amino acid substitutions are substitutions within the following five groups of amino acids:

Group 1: F Y W

Group 2: V L I

Group 3: H K R

Group 4: M S T P A G

Group 5: D E

Fragments or analogues of the peptides of the invention may be screened for their effectiveness by raising antibodies thereto in a suitable animal, as described herein, and screening the antibodies for their ability to neutralize the proteolytic activity of elastase, as described herein.

3. Antibodies

The peptides of the invention may be coupled to a carrier protein to increase immunogenicity for antibody production. For example, the peptides of the invention may be coupled to bovine serum albumin or keyhole limpet haemocyanin.

In order to prepare peptides for production of polyclonal antibodies, fusion proteins containing a selected peptide, such as peptide 15 or peptide 42, can be synthesized in bacteria by expression of corresponding DNA sequences in a suitable cloning vehicle. Fusion proteins are commonly used as a source of antigen for producing antibodies. Two widely used expression systems for *E. coli* are lacZ fusions using the pUR series of vectors and trpE fusions using the pATH vectors. The peptides can then be purified, coupled to a carrier protein if desired, and mixed with Freund's adjuvant (to help stimulate the antigenic response of the animal) and injected into rabbits or other appropriate laboratory animals.

Following booster injections at weekly intervals, the rabbits or other laboratory animals are bled and ther serum isolated. The serum can be used directly or the polyclonal antibodies purified prior to use by various methods including affinity chromatography.

As will be understood by those skilled in the art, monoclonal antibodies may also be produced using the peptides of the invention. A selected peptide, coupled to a carrier protein if desired, is injected in Freund's adjuvant into mice. After being injected three times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened by ELISA to identify those containing cells making binding antibody. These are then plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant techniques in which plasmids are generated which express the desired monoclonal antibody fragment in a suitable host.

Antibodies to the peptides of the invention may be administered to a subject in acute situations to provide passive immunization. For example, acute infection by a zinc metalloprotease-secreting pathogen in cancer patients or burn patients may be treated by passive immunization.

Antibodies to the peptides of the invention, including antibodies to peptides 15 and 42, are also useful for identification of microorganism strains, enabling the identification of bacterial strains which secrete metalloproteases.

4. Assays

The peptides of the invention, including peptides 15 and 42 and analogues and fragments thereof are also useful as antigens in immunoassays including enzyme-linked immunosorbent assays (ELISA), radioimmunoassays (RIA) and other non-enzyme linked antibody binding assays or procedures known in the art for the detection and assay of these peptides.

EXAMPLES

The examples are described for the purposes of illustration and are not intended to limit the scope of the invention.

Methods of molecular genetics, protein and peptide biochemistry and immunology referred to but not explicitly described in this disclosure and examples are reported in the scientific literature and are well known to those skilled in the art.

Materials and Methods

Proteases

Elastase and alkaline protease, prepared from *P. aeruginosa*, were purchased from Nagase Biochemicals Inc. (Osaka, Japan). *V. cholerae* HA/protease was provided by Dr. R. A. Finkelstein (University of Missouri-Columbia School of Medicine, Columbia, Miss.). Thermolysin from *B. thermoproteolyticus* and the Serratia metalloprotease (SMP) from *S. marcescens* were purchased from Sigma Chemical Co. St. Louis, Mo. PSCP was purified as previously described (36).

Monoclonal Antibodies and Purification

MAbs (36–6-6, 36-6-8, 36-1-5, 36-5-15, and 36-9-19) to PSCP were prepared as previously described in Reference 7 which is incorporated herein by reference. MAbs were purified using the Pierce IgM purification kit as recommended by the manufacturer.

NCS Digestion of Elastase

Elastase was digested with N-chlorosuccinimide (NCS; Aldrich) as previously described (37). Elastase (0.1 mg) was mixed with 0.15 g urea, 150 µl acetic acid and 50 µl 0.11 M NCS for a final concentration of 0.012 M NCS and digested for 30 min at room temperature. Reactions were stopped by the addition of 20% cold trichloroacetic acid. Samples were precipitated at −20° C. for at least one hour and centrifuged at 10,000 X g for 30 min at 4° C. The resultant pellets were washed two times with ethanol:ether (1:1) and dried under vacuum. The dried pellets were resuspended in 1X sample buffer and separated by tricine gel (16%) electrophoresis (38).

SDS-PAGE and Immunoblotting

SDS-PAGE was performed on 12.5% polyacrylamide gels by the method of Laemmli (39). Gels were either stained with Coomassie brilliant blue R-250 (Sigma) (0.25% Coomassie, 25% methanol, and 10 acetic acid) or electrophoretically blotted by the method of Towbin et al. (9). Blots were reacted with antibodies as previously described (7).

Epitope Mapping

Sixty 9-mer overlapping peptides, with a two amino acid offset, encompassing the 13.9 kDa NCS-elastase fragment, were synthesized on pins using an epitope scanning kit, as suggested by the manufacturer (Chiron Mimotopes, Australia). Two additional control peptides were synthesized. PLRQ was a positive control for the antibody (Ab) provided by the manufacturer, and GLAQ was a negative control. Two additional control peptide pins were provided with the kit. Peptides were tested for recognition by the five purified MAbs to PSCP (1:100 dilution) by ELISA as suggested by the manufacturer. An unrelated control MAb (#6), to P. aeruginosa ferripyochelin binding protein(40), did not react with any of the peptides. After each test, the MAb was stripped from the peptide pin by sonication in 0.1 M phosphate buffer, 1% SDS (w/v), 0.1% 2-mercaptoethanol (v/v) for 10 min followed by washing two times in dH$_2$O at 60° C. for 30 sec. Peptide pins were then washed for 30 min in dH$_2$O initially at 60° C., immersed in boiling methanol for at least 15 sec and air dried. Removal of the MAb was confirmed by testing the peptide pins with conjugate as described by the manufacturer.

Polyclonal Antibody Production

Peptides HGFTEQNSG (peptide 15) and LRYM-DQPSRD (peptide 42) and the same peptides conjugated to bovine serum albumin (BSA) or keyhole limpet hemocyanin (KLH) were synthesized by the Alberta Peptide Institute, Edmonton, Canada. Conjugates were prepared for immunization as suggested by the manufacturer. The BSA conjugates were prepared in complete Freund's adjuvant and 0.5 ml containing 0.1 mg of either peptide 15-BSA or peptide 42-BSA was injected in each thigh of two New Zealand white rabbits. Rabbits immunized with peptide 42-BSA were boosted with intramuscular injections of peptide in incomplete Freund's three times at bi-weekly intervals. Rabbits immunized with peptide 15-BSA were given two additional boosts as test bleeds indicated lower titres.

ELISA

To determine the antibody titres, 96-well plates were coated with either the BSA-peptide conjugate or the KLH-peptide conjugate (1 µl/well). Use of the heterologous conjugate was used to indicate whether the antibodies present were due to peptide antibodies or BSA antibodies or both. The assay was performed as previously described (7).

Neutralization Assays

For neutralization assays, protease was preincubated with 10 mM Tris-HCl, pH 8.0, pre-immune rabbit serum, anti-peptide 15 serum or anti-peptide 42 serum at a dilution of 1:500 for 1 hour at 37° C. One ml was transferred to a microfuge tube containing 20 mg hide powder azure (Sigma) and 0.5 ml 10 mM Tris-HCl, pH 8.0. The samples were incubated for 2 h at 37° C. with shaking, centrifuged and the $A_{595}$ was measured. Assays were conducted in triplicate (7).

ELISA to Measure Antibody Affinity

To compare the affinity of antibodies to peptide 15 and peptide 42 for the various proteases employed, an ELISA was performed. Immulon 4 96-well microtiter plates (Dynatech) were coated with 100 µl of each protease (1 µg/ml) in carbonate coating buffer (pH 9.6) for 2 h at 37° C. The plates were washed with buffer A (phosphate-buffered saline, pH 7.4, 0.05% (w/v) BSA) and blocked for 2 hr at 37° C. by the addition of 250 µl/well PBS, 5% BSA. Following two washes with buffer A, serial two-fold dilutions, starting at 1:100 of anti-peptide 15 or anti-peptide 42 rabbit serum in buffer A (100 µl/well), were applied to the wells. All assays were performed in duplicate and included negative controls in which no antibody was present. After a two hr incubation at 37° C., the plates were washed five times with buffer A. Protein A-peroxidase conjugate (100 µl, 1:2000; Sigma) was added to each well and incubated at 37° C. for 2 hr. Wells were washed five times with buffer A and aspirated thoroughly. ABTS substrate (100 µl/well, BioRad) was applied to each well and after agitation at room temperature for 15 min, the $A_{405}$ was determined using an EL340 BioKinetics Reader (Bio-Tek Instruments).

Example 1

Mapping of P. aeruginosa Elastase Epitopes

In order to determine which epitopes are recognized by elastase neutralizing MAbs, overlapping peptides were synthesized based on the sequence of P. aeruginosa elastase. Polyclonal antisera were raised against the peptides corresponding to the mapped epitopes to determine whether the anti-peptide antibodies (Abs) could neutralize various metalloproteases.

Recognition of NCS-elastase Fragments by MAbs

Chemical cleavage of P. aeruginosa elastase followed by immunoblot analysis was used to localize the epitope recognized by the neutralizing MAbs. The chemical N-chlorosuccinimide (NCS), which cleaves after Trp residues, was used to digest elastase. Complete digestion of elastase with NCS would result in fragments of 9.9, 3.0, 13.9, 2.2 and 4.3 kDa (in order from the N-terminus). Incomplete digestion of elastase was obtained, resulting in fragments of 26.5, 21.5, 19, 16.5, 14, 10 and 4 kDa (FIG. 3A). MAb 36-6-8 was found to recognize fragments of 26.5, 21.5, 19, 16.5 and 14 kDa on immunoblots (FIG. 3B). None of the fragments smaller than 14 kDa reacted with the MAb. MAb 36-6-6 was found to recognize the same fragments (data not shown). This pattern of recognition suggests that these MAbs recognize the 13.9 kDa NCS fragment of elastase as well as larger partially digested fragments which contain the 13.9 kDa fragment and one or more of the adjacent fragments. Complete digestion was not sought since higher NCS to elastase molar ratios can lead to oxidation and cleavage of methionine and cysteine residues.

Epitope Mapping of the 13.9 kDa NCS-elastase Fragment

Sixty overlapping 9-mer peptides, with a two amino acid offset, were synthesized spanning the 13.9 kDa NCS-elastase fragment. The first peptide was DGTAMLFGD and the last was YLLANSPGW. In addition, two control peptides were synthesized, PLRQ (positive) and GLAQ (negative). Essentially the same results were found with all five antibodies. The results with two representative antibodies, Mabs 36-6-6 and 36-6-8, are shown in FIG. 1. MAbs 36-6-6 and 36-6-8 bound most strongly to peptides 15 ($_{341}$HGFTEQNSG$_{349}$) and 42 ($_{395}$RYMDQPSRD$_{403}$). Numbering of the amino acids is from the elastase precursor. Peptides with sequences overlapping these peptides were also recognized to a lesser degree. Two control peptide pins were provided with the kit and these peptides responded as expected with the control antibody provided (see FIG. 1).

Example 2

Polyclonal Antibodies to Identified Epitopes

Characterization of Polyclonal Antibodies to Peptides 15 and 42

Polyclonal antibodies to peptides 15 and 42 were obtained by immunizing rabbits with peptide 15 or 42 conjugated to BSA. Using peptides 15 and 42 conjugated to KLH as the coating antigen in ELISAs, peptide 15 and peptide 42 antisera had titres greater than 1:12,000 (Table 2). Both peptide 15 and peptide 42 antisera recognized intact elastase on immunoblots (FIGS. 4A and 4B) or ELISA (FIGS. 5A and 5B).

MAbs 36-6-6 and 36-6-8 were previously reported to react with other bacterial metalloproteases, including thermolysin, P. aeruginosa alkaline protease, V. cholerae HA/protease, B. cepacia 40 kDa protease, and S. marcescens SMP (7,29). To determine if this crossreactivity was due to a recognition of conserved sequences corresponding to either peptide 15 or 42, the ability of antiserum to peptide 15 and antiserum to peptide 42 to crossreact with these metalloproteases was examined on immunoblots (FIGS. 4A and 4B).

Proteases were separated by SDS- (12.5%) PAGE, blotted onto immobilon membranes and reacted with either peptide 15 (FIG. 4A) or peptide 42 (FIG. 4B). Peptide 15 antiserum was diluted 1:1,000 for reactions with elastase and 1:100 for reactions with the other metalloproteases. Peptide 42 antiserum was diluted 1:20,000 for reactions with elastase and 1:1,000 for reactions with other metalloproteases.

Antiserum to peptide 15 or peptide 42 reacted weakly with other bacterial metalloproteases even at 10–20 fold higher antibody concentrations than used for elastase. A 1:100 dilution of antiserum to peptide 15 reacted strongly with HA/protease (FIG. 4A, lane 3) and faintly with alkaline protease (FIG. 4A, lane 4). Antipeptide 15 serum did not react with SMP, thermolysin, PSCP or the B. cepacia 40 kDa protease on immunoblots. Antiserum to peptide 42 at a 1:1000 dilution reacted strongly with HA/protease (FIG. 4B, lane 3) and more weakly with thermolysin, PSCP, and B. cepacia 40 kDa protease (FIG. 4B, lanes 6,7, and 8, respectively). Antipeptide 42 serum did not recognize alkaline protease nor SMP on these blots. Therefore, both antipeptide sera were capable of recognizing other metalloproteases, but they differed with respect to their reactions with these proteases on immunoblots.

Figure 5:
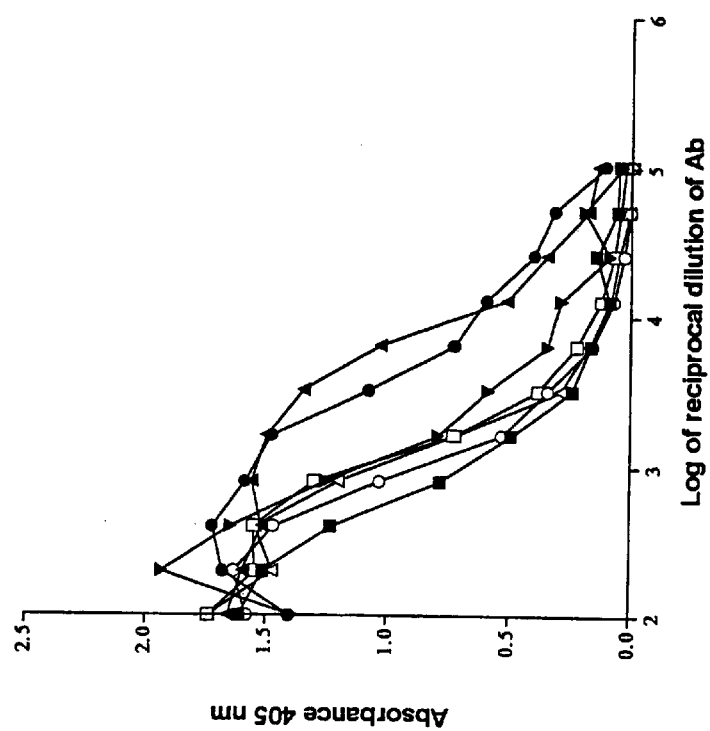
Figure 5:
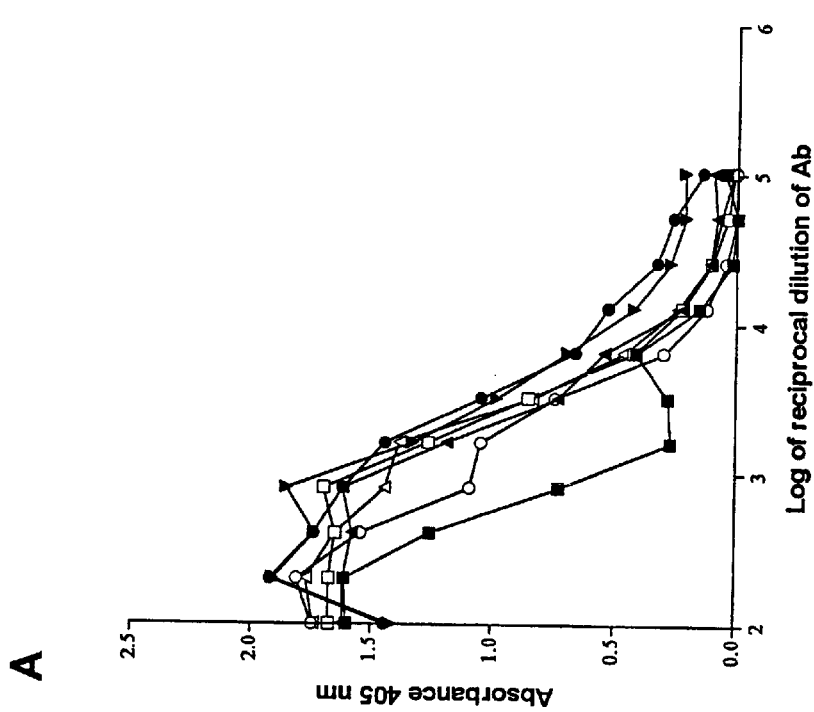

Previously, the affinity of MAb 36-6-8 for various metalloproteases was estimated by comparing the dose response curves of this MAb, using the same concentration of each protease, in an ELISA (29). To determine if the antipeptide antibodies could react with non-denatured forms of the metalloproteases examined above, a similar assay was performed (FIG. 5). Microtiter plates were coated with 0.1 µg/well protease, reacted with serial two-fold dilutions of anti-peptide sera starting at a 1:100 dilution and processed as described above. The antisera to peptide 15 and peptide 42 both reacted in the ELISA with all the proteases examined. Antiserum to peptide 15 had a similar affinity for all the proteases examined, with the exception of PSCP, which appeared to be lower than the others (FIG. 5A). Therefore, for antiserum to peptide 15, there was not a correlation between the results obtained with immunoblots of proteins denatured on SDS-PAGE and non-denatured proteins examined by ELISA. Antiserum to peptide 42 had a greater affinity for elastase and HA/protease in this assay as the absorbance at 405 nm was generally 2–3 fold higher for these two proteases at most dilutions in the linear portion of the binding curve (FIG. 5B). To achieve an absorbance between 0.5 and 1.3 in this assay required about one log less antibody when the plates were coated with elastase or HA/protease than with the other enzymes.

Neutralization of Protease Activity

The MAbs used to identify the epitopes corresponding to peptides 15 and 42 have been shown to neutralize thermolysin type metalloproteases but not serralysin proteases (29). The antipeptide polyclonal sera were examined for their ability to neutralize the activity of these metalloproteases, as described above, to determine if one epitope was responsible for inducing the production of neutralizing antibodies. Both peptide 15 and peptide 42 antisera were able to reduce the proteolytic activity of P. aeruginosa elastase, B. cepacia PSCP, thermolysin and V. cholerae HA/protease to low levels. The antisera did not inhibit alkaline protease or Serratia metalloprotease activity (Table 3).

Example 3

Immunization with Peptide 15 and Peptide 42

Seventy eight seven-week old Sprague-Dawley rats were immunized subcutaneously with 50 µg of peptide 15 or peptide 42 conjugated to KLH (15-KLH or 42-KLH) and boosted three times at two week intervals with 25 µg of the appropriate conjugate. Control rats were injected with saline plus adjuvant. Three rats from each group were bled six days after each boost and the presence of anti-peptide antibodies determined. After the second boost, 2/3 of each of the immunized groups had anti-peptide antibodies. After boost three, 3/3 rats in each of the immunized groups had anti-peptide antibodies. The mean antibody titres to peptides 15 and 42 were 1:128,000 and 1:1600, respectively, as determined by ELISA against the same peptide conjugated to BSA.

Rats were infected intratracheally using the agar bead model of Cash et al. (41) with a wild type strain of P. aeruginosa (PAO). At three and seven days after infection, the lungs of five rats in each group with lavaged with BSA. An aliquot of lavage was used to determine the PMN differential count and the remainder frozen at −70° C. On day seven, quantitative bacteriology (41) was performed on five rats from each group and quantitative pathology (42) on 5–7 rats from each group.

The PMN differential count (PMNs/WBCs) in the BAL (bronchial alveolar lavage) was significantly reduced in rats immunized with either peptide 15 or peptide 42 on day 3 compared to non-immunized rats and significantly lower in rats immunized with peptide 42 on day 7 compared to non-immunized rats, as shown in Table 4.

These data show that immunization with either peptide reduces the inflammatory response in the lungs. Even though the serum antibody titres were lower to peptide 42 than 15, peptide 42 immunization was at least as effective in reducing the PMN infiltration in the lung.

Quantitative bacteriology was performed on five animals in each group on day 7. The mean values were $2.0 \times 10^6$ cfu/ml for the controls, $5.7 \times 10^5$ and $1.3 \times 10^6$ for animals immunized with peptide 15 and 42, respectively. Although the mean numbers of PAO recovered from the lungs was not significantly different, 2/5 animals in each of the groups immunized with peptide-conjugates had completely cleared the bacteria. All of the control animals remained infected. Quantitative pathology was performed on haematoxylin and eosin stains of sagittal slices of the left lobe of formalin fixed lungs by the method of Dunnill (42).

The degree of pathology observed in the immunized animals was 40–50% less than that of control animals as shown in Table 5. 3/7 rats immunized with peptide 42 had 3% or less pathology, and 1/5 rats immunized with peptide 15 had 8% pathology. The lowest amount of infiltration in the control group, however, was 18% and 4/6 control rats had>44% pathology.

Example 4

Antibodies to Neutralizing Epitopes in CF Patients

Numerous studies have reported that CF patients produce high levels of antibodies but most often these are not functional antibodies. Studies were carried out to determine if CF patients produce antibodies to the peptides identified as neutralizing epitopes. Sera from 84 CF patients taken at their most recent clinic visit were examined by ELISA to determine their antibody titre to *P. aeruginosa* elastase, peptide 15- or 42- BSA conjugate or peptide 15- or 42- KLH conjugate. Pooled normal human serum was used as a control. Titres were considered positive if the $A_{450}$ was at least twice the backgound of the normal human serum pool. 62 of the 84 sera (74%) were positive for anti-elastase antibodies. Four patients (5%) had antibodies detectable by ELISA to both peptides 15 and 42, irrespective of whether the peptide was conjugated to BSA or KLH, indicating that these antibodies recognized the peptide 15 or 42 portion of the conjugate. These four patients had titres of 1:500 or greater to the peptides, whereas the mean titre to elastase was 1:4000–8000 in the positive patients and several patients had titres greater than 1:32,000. The four sera with detectable anti-peptide antibodies showed neutralising activity against the proteolytic activity of *P. aeruginosa* elastase. This study confirms that humans do make antibodies to these epitopes, but at a lower frequency and at a lower titre than to elastase.

The present invention is not limited to the features of the embodiments described herein, but includes all variations and modifications within the scope of the claims.

REFERENCES

1. Wretlind, B., and O. R. Pavlovskis (1983), *Rev. Infect. Dis.* 5(Suppl.): 998–1004.

2. Hong, Y. Q., and Ghebrehiwet, B. (1992), *Clin. Immunol. Immunopathol.* 62:133–138.

3. Horvat, R. T. and M. J. Parmely (1988), *Infect. Immun.* 56:2925–2932.

4. Kessler, E., M. Safrin, J. C. Olson and D. E. Ohman (1993), *J. Biol. Chem.* 268:7503–7508.

5. Olson, J. C. and D. E. Ohman (1992), *J. Bacteriol.,* 174:4140–4147.

6. Toder, D. S., S. J. Ferrell, J. L. Nezezon, L. Rust, and B. H. Iglewski (1994), *Infect. Immun.* 62:1320–1327.

7. Kooi, C., A. Cox, P. Darling, and P. A. Sokol (1994), *Infect. Immun.,* 62:2811–2817.

8. Bever, R. A., and B. H. Iglewski (1988), *J. Bacteriol.,* 170:4309–4314.

9. Towbin, H., T. Staehelin, and J. Gordon (1979), *Proc. Natl. Acad. Sci. USA,* 76:4350–4354.

10. Booth, B. A., M. Boesman-Finkelstein, and R. Finkelstein, (1983), *Infect. Immun.,* 42:639–644.

11. Finkelstein, R. A., M. Boseman-Finkelstein, and P. Holt, (1983), *Proc. Natl. Acad. Sci. USA,* 80:1092–1095.

12. Hase, C. C., and R. A. Finkelstein, (1990), *Infect. Immun.,* 58:5011–4015.

13. Hase, C. C., and R. A. Finkelstein, (1991), *J. Bacteriol.,* 173:3311–3317.

14. Hase, C. C., and R. A. Finkelstein, (1993), *Microbiol. Reviews,* 57:823–837.

15. Gilligan P. H. (1991), *Clin. Microbiol. Rev.,* 4:35–51.

16. Pegues, D. A., L. A. Carson, R. L. Anderson, M. J. Norgard, T. A. Argent, W. R. Jarvis, and C. H. Woernle, (1993), *6i Clin. Infect. Dis.,* 16:407–11.

17. Taylor, R. F. H., H. Gaya and M. E. Hodson, (1993), *Resp. Medicine,* 87:187–192.

18. McKevitt, A. L. and D. E. Woods (1984), *J. Clin. Micro.,* 19:291–293.

19. McKevitt, A. L., S. Bajaksouzian, J. D. Klinger, and D. E. Woods, (1989), *Infect. Immun.,* 57:771–778.

20. Fick, R. B. Jr., R. S. Baltimore, S. U. Squier, and H. R. Reynolds, (1985), *J. Inf. Dis.,* 151:589–598.

21. Bainbridge, T. and R. B. Fick, Jr., (1989), *J. Clin. Lab. Med.,* 114:728–733.

22. Horvat, R. T., M. Clabaugh, C. Duval-Jobe, and M. J. Parmely, (1989), *Infect. Immun.,* 57:1668–1674.

23. Klinger, J. D., D. C. Straus, C. B. Hilton, and J. A. Bass, (1978), *J. Inf. Dis.,* 138:49–58.

24. Jagger, K. S., D. L. Robinson, M. N. Franz, and R. L. Warren (1982), *J. Clin. Micro.,* 15:1054–1058.

25. Doring, G., H. J. Obernesser, K. Botzenhart, B. Flehmig, N. Hoiby, and A. Hofmann, (1983), *J. Inf. Dis.,* 147:744–750.

26. Hollsing, A. E., M. Granstrom, M. L. Vasil, B. Wretlind, and B. Strandvik, (1987), *J. Clin, Mocrobiol.,* 25:1868:1874.

27. Granstrom, M., A. Ericsson, B. Strandvik, B. Wretlind, O. R. Pavloskis, R. Berka, and M. L. Vasil, (1984), *Acta. Paediatr. Scand.,* 73:772–777.

28. Jongeneel, C. V., J. Bouvier, and A. Bairoich, (1989), *FEBS Lett.,* 242:211–214.

29. Kooi, C., and P. A. Sokol, (1996), *J. Med. Microbiol.,* In Press.

30. Thayer, M. M., K. M. Flaherty and D. B. McKay, (1991), *J. Biol . Chem.,* 266:2864–2871.

31. O'Hagan (1992), *Clin. Pharmacokinet,* 22:1.

32. Ulmer et al., 91993), *Curr. Opinion Invest. Drugs,* 2(9):983.

33. Lockhoff et al., (1991), *Chem. Int. Ed. Engl.,* 30:1611.

34. Wiesmuller et al., (1989), *Vaccine,* 8:29.

35. Deres et al., (1989), *Nature,* 342:651.

36. McKevitt, A. I., S. Bajaksouzian, J. D. Klinger, and D. E. Woods (1989), *Infect. Immun.,* 57:771–778.

37. Lischwe, M. A. and M. T. Sung, (1977), *J. Biol. Chem.,* 252:4976–4980.

38. Schagger, H. and G. Von Jagow, (1987), *Anal. Biochem.,* 166:368–379.

39. Laemmli, V. K., (1970), *Nature (London),* 277:680–685.

40. Sokol, P. A., and D. E. Woods (1986), *Infect. Immun.,* 53:621–627.

41. Cash, H. A., D. E. Woods, B. McCullough, W. G. Johanson, Jr. and J. A. Bass, (1979), *Am. Rev. Resp. Dis.,* 119:453–459.

42. Dunnill, M. S. (1962), *Thorax,* 17:320–328.

TABLE 2

ELISA titers of sera raised against peptide 15- and 42-
BSA conjugates, tested against peptide 15- or 42- KLH
conjugates as antigen

| Antisera | to Peptide 15-KLH | to Peptide 42-KLH |
|---|---|---|
| anti-peptide 15-BSA | 1:12,800 | 1:6400 |
| anti-peptide 42-BSA | 1:3200 | 1:51,200 |

TABLE 3

Comparison of the ability of antiserum to peptide 15 and peptide 42 to neutralize proteolytic activity

| | Proteolytic Activity[a] | | |
|---|---|---|---|
| Protease | Peptide 15 Antiserum | Peptide 42 Antiserum | Control Rabbit Serum |
| Thermolysin | 2 ± 3[b] | 3 ± 1[b] | 85 ± 13 |
| *V. cholerae* HA/protease | 12 ± 17[b] | 10 ± 13[b] | 121 ± 7 |
| *P. aeruginosa* Elastase | 2 ± 1[b] | 15 ± 9[b] | 88 ± 1 |
| *B. cepacia* PSCP | 4 ± 0.1[b] | 4 ± 3[b] | 135 ± 13 |
| *P. aeruginosa* Alkaline Protease | 88 ± 2 | 100 ± 5 | 103 ± 3 |
| Serratia metalloprotease | 89 ± 6 | 105 ± 1 | 110 ± 16 |

[a]Proteolytic activity was expressed as a percentage of the control (100%) which contained no sera.
[b]Significantly different (p <0.001) than reactions containing no Ab using Bonferroni Multiple Comparisons Test.

TABLE 4

| | DAY 3 | | DAY 7 | |
|---|---|---|---|---|
| TREATMENT | % PMN[a] | p value[b] | % PMN | p value[b] |
| control | 48.6 ± 11.6 | — | 17.0 ± 3.7 | — |
| peptide 15 | 16.4 ± 11.9 | .001* | 14.2 ± 12.0 | .33 |
| peptide 42 | 27.8 ± 13.7 | 0.32* | 6.0 ± 5.3 | .01* |

[a]% PMNs in total WBC count
[b]compared to control, two-tailed t test for unpaired observations.
*significantly different from control.
No significant difference between peptide 15 and peptide 42 immunized animals on either day 3 or day 7.

TABLE 5

| Treatment | n | % Pathology (mean ± sd) | % Pathology Range |
|---|---|---|---|
| Control | 6 | 44.2 ± 22.1 | 18–78 |
| Peptide 15 | 5 | 25.0 ± 10.0 | 8–33 |
| Peptide 42 | 7 | 22.3 ± 20.1 | 3–46 |

We claim:

1. A peptide consisting of the amino acid sequence VSHGFTEQNSGLIYRGQSGGMNEAF (Sequence ID No: 1) or a fragment or conservative amino acid substitution variant thereof, which contains an epitope which is recognized by an antibody which neutralizes the proteolytic activity of *Pseudomonas aeruginosa*.

2. The peptide or fragment or variant of claim 1 wherein the peptide or fragment or variant is a peptide having an amino acid sequence comprising at least nine consecutive amino acids from the amino acid sequence VSHGIFTEQNSGLIYRGQSGGMNEAF (Sequence ID No: 1).

3. The peptide or fragment or variant of claim 1 wherein the peptide or fragment or variant is a fragment selected from the group consisting of
    (a) VSHGPTEQN (Sequence ID No:2);
    (b) HGFTEQNSG (Sequence ID No:3);
    (c) FTEQNSGLI (Sequence ID No:4);
    (d) EQNSGLIYR (Sequence ID No:5);
    (e) NSGLIYRGQ (Sequence ID No:6);
    (f) GLIYRGQSG (Sequence ID No:7);
    (g) IYRGQSGGM (Sequence ID No:8);
    (h) RGQSGGMNE (Sequence ID No:9);

(i) QSGGMNEAF (Sequence ID No:10).

4. A peptide consisting of the amino acid sequence HGFTEQNSG (Sequence ID No:3).

5. A peptide consisting of the amino sequence SGALRYMDQPSRDGRSIDM (Sequence ID No: 11) or a fragment or conservative amino acid substitution variant thereof, which contains an eptitope which is recognized by an antibody which neutralizes the proteolytic activity of *Pseudomonas aeruginosa*.

6. The peptide or fragment or variant of claim 5 wherein the peptide or fragment or variant is a peptide having an amino acid sequence comprising at least nine consecutive amino acids from the amino acid sequence SGALRYMDQPSRDGRSIDM (Sequence ID No: 11).

7. The peptide or fragment or variant of claim 5 wherein the peptide or fragment or variant is a fragment selected from the group consisting of
(a) SGALRYMDQ (Sequence ID No: 12);
(b) ALRYMDQPS (Sequence ID No: 13);
(c) RYMDQPSRD (Sequence ID No:14);
(d) MDQPSRDGR (Sequence ID No:15);
(e) QPSRDGRSI (Sequence ID No: 16);
(f) SRDGRSIDM (Sequence ID No: 17).

8. A peptide consisting of the amino acid sequence RYMDQPSRD (Sequence IN No:14).

9. An immunogenic composition comprising at least one active component selected from the group consisting of:
(a) a peptide consisting of the amino acid sequence HGFTEQNSG (Sequence ID No:3);
(b) a peptide consising of the amino acid sequence RYMDQPSRD (Sequence ID No:4);
(c) a peptide consisting of the amino acid sequence VSHGFTEQNSGLIYRGQSGGMNEAF (Sequence ID No:1);
(d) a peptide consisting of the amino acid sequence SGALRYMDQPSRIDGRSIDM (Sequence ID No.:11); and
(e) a fragment or conservative amino acid substitution variant of a peptide of (a), (b), (c) or (d), which contains a epitope which is recognized by an antibody which neutralizes the proteolytic activity of *Pseudomonas aeruginosa* and a pharmaceutically acceptable carrier, said at least one active component producing an immune response when administered to a host.

10. The immunogenic composition of claim 9 formulated as a vaccine for administration to a mammal to protect the mammal against a disease caused by a bacterial pathogen which secretes a zinc metalloprotease.

11. The immunogenic composition of claim 10 wherein the bacterial pathogen secretes a thermolysin-like metalloprotease.

12. The inmmunogenic composition of claim 10 wherein the mammal is to be protected against a disease caused by a pathogen selected from the group consisting of *Pseudomonas aeruginosa, B. cepacia, Vibrio cholerae, V. vulnificus, Legionella pneumophila, Serratia marcescens, Bacillus anthracis, Clostridium tetani, Clostridium botulinum, Aeromonas hydrophilia, Staphylococcus epidermidis, Staphylococcus aureus, Streptococcus sanguis, Streptococcus faecalis, Lysteria monocytogenes,* and *Pasteurella haemolytica*.

13. The immunogenic composition of claim 12 wherein the at least one active component is selected from the group consisting of
(a) the peptide HGFTEQNSG (Sequence ID No:3);
(b) the peptide RYMDQPSRD (Sequence ID No:14);
(c) a mixture of the peptide HGFTEQNSG (Sequence ID No:3), and the peptide RYMDQPSRD (Sequence ID No:14).

14. The immunogenic composition of claim 13 wherein the peptide is conjugated to a carrier protein.

15. The immunogenic composition of claim 14 wherein the carrier protein is selected from the group consisting of keyhole limpet haemocyanin, diphtheria toxoid, diphtheria toxin CRM197, tetanus toxoid, *P. aeruginosa* exotoxin A mutant form, cholera toxin B subunit, pertussis toxin subunits, measles virus F protein and Haemophilus PRP outer membrane protein.

* * * * *

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Val Ser His Gly Phe Thr Glu Gln Asn Ser Gly Leu Ile Tyr Arg Gly
1               5                   10                  15

Gln Ser Gly Met Asn Glu Ala Phe
            20              25

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Val Ser His Gly Phe Thr Glu Gln Asn
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

His Gly Phe Thr Glu Gln Asn Ser Gly
1               5

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Phe Thr Glu Gln Asn Ser Gly Leu Ile
1               5

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Glu Gln Asn Ser Gly Leu Ile Tyr Arg
1               5

(2) INFORMATION FOR SEQ ID NO:6:

(i) SEQUENCE CHARACTERISTICS:
        (A) LENGTH: 9 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:6:

Asn Ser Gly Leu Ile Tyr Arg Gly Gln
1               5

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Gly Leu Ile Tyr Arg Gly Gln Ser Gly
1               5

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ile Tyr Arg Gly Gln Ser Gly Gly Met
1               5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Arg Gly Gln Ser Gly Gly Met Asn Glu
1               5

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gln Ser Gly Gly Met Asn Glu Ala Phe
1               5

(2) INFORMATION FOR SEQ ID NO:11:

(i) SEQUENCE CHARACTERISTICS:
        (A) LENGTH: 19 amino acids
```

(B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Ser Gly Ala Leu Arg Tyr Met Asp Gln Pro Ser Arg Asp Gly Arg Ser
1               5                   10                  15

Ile Asp Met (2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Ser Gly Ala Leu Arg Tyr Met Asp Gln
1               5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ala Leu Arg Tyr Met Asp Gln Pro Ser
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Arg Tyr Met Asp Gln Pro Ser Arg Asp
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Met Asp Gln Pro Ser Arg Asp Gly Arg
1               5

(2) INFORMATION FOR SEQ ID NO:16:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Gln Pro Ser Arg Asp Gly Arg Ser Ile
1               5

(2) INFORMATION FOR SEQ ID NO:17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Ser Arg Asp Gly Arg Ser Ile Asp Met
1               5

(2) INFORMATION FOR SEQ ID NO:18:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Asp Gly Thr Ala Met Leu Phe Gly Asp
1               5

(2) INFORMATION FOR SEQ ID NO:19:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:19:

Tyr Leu Leu Ala Asn Ser Pro Gly Trp
1               5

(2) INFORMATION FOR SEQ ID NO:20:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:20:

Arg Tyr Phe Asp Gln Pro Ser Arg Asp
1               5

```
(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

His Ala Val Thr Asp Tyr Thr Ala Gly
1               5

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Arg Ser Met Ser Asp Pro Ala Lys Tyr
1               5

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Asn Gly Gly Val His Ile Asn Ser Gly
1               5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Val Tyr Thr Pro Gly Ile Ser Gly Asp
1               5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Ser Tyr Trp Glu Glu Gln Asn Thr Gly
1               5
```

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Ala Tyr Ser Ser Ala Pro Leu Leu Asp
1           5

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Ile Thr Phe Thr Glu Val Ala Ala Gly
1           5

(2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Leu Tyr Gly Ala Asn Pro Ser Thr Arg
1           5

(2) INFORMATION FOR SEQ ID NO:29:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

His Tyr Ala Ala Ala Pro Leu Leu Asp
1           5